US010145192B1

(12) United States Patent
Kelley et al.

(10) Patent No.: US 10,145,192 B1
(45) Date of Patent: *Dec. 4, 2018

(54) SOIL SAMPLING ASSEMBLY

(71) Applicant: Soil Analytics, LLC, Winterset, IA (US)

(72) Inventors: Jay T. Kelley, Winterset, IA (US); Matthew J. Rasmussen, Fremont, NE (US)

(73) Assignee: SOIL ANALYTICS, LLC, Winterset, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/395,691

(22) Filed: Dec. 30, 2016

Related U.S. Application Data

(63) Continuation of application No. 14/486,058, filed on Sep. 15, 2014, now Pat. No. 9,534,464.

(60) Provisional application No. 61/877,507, filed on Sep. 13, 2013.

(51) Int. Cl.
| | |
|---|---|
| *E21B 25/00* | (2006.01) |
| *G01N 1/08* | (2006.01) |
| *E21B 21/01* | (2006.01) |
| *E21B 10/44* | (2006.01) |
| *G01N 33/24* | (2006.01) |

(52) U.S. Cl.
CPC ............ *E21B 25/005* (2013.01); *E21B 10/44* (2013.01); *E21B 21/01* (2013.01); *E21B 25/00* (2013.01); *G01N 1/08* (2013.01); *G01N 33/24* (2013.01); *G01N 2033/245* (2013.01)

(58) Field of Classification Search
CPC .. G01N 1/02; G01N 1/04; G01N 1/08; G01N 1/28; G01N 33/24; G01N 2033/245; E21B 10/44; E21B 25/00; E21B 25/005

USPC ....... 73/864, 864.41, 684.43, 864.44, 864.91
See application file for complete search history.

(56) References Cited

U.S. PATENT DOCUMENTS

| | | | |
|---|---|---|---|
| 1,362,968 | A | 12/1920 | Stewart |
| 2,565,224 | A | 7/1948 | Gibbens |
| 3,084,553 | A | 4/1963 | Cullinan et al. |
| 3,224,512 | A | 12/1965 | Alexander |
| 3,331,249 | A | 7/1967 | Boxrud |
| 3,391,543 | A | 7/1968 | Sweeney et al. |
| 3,464,504 | A | 9/1969 | Stange |
| 3,625,296 | A | 12/1971 | Mabry |
| 4,316,393 | A | 2/1982 | Philipenko |
| RE30,901 | E | 4/1982 | Boxrud |

(Continued)

FOREIGN PATENT DOCUMENTS

DE 3621409 A1 1/1988

*Primary Examiner* — Benjamin Schmitt
(74) *Attorney, Agent, or Firm* — Mallory M. Henninger; Advent, LLP

(57) ABSTRACT

A soil sampler assembly includes a utility vehicle and a soil sampler module coupled to the utility vehicle. The utility vehicle includes a cab, and the soil sampler module is configured to deposit a soil sample in the cab. For example, the soil sampler assembly includes a conveyor system configured to convey the soil sample to the cab. The conveyor system includes a central conveyor and a lateral conveyor that feeds the central conveyor. The central conveyor is on a travel track. The soil sampler assembly further includes a sampler arm assembly. The sampler arm assembly includes a power cylinder, a guide cylinder, a transfer block, and a probe. The probe has a tip, and the tip of the probe includes an outer surface defining an outer taper bore and an inner surface defining an inner taper bore.

16 Claims, 19 Drawing Sheets

(56) References Cited

U.S. PATENT DOCUMENTS

| | | |
|---|---|---|
| 4,332,301 A | 6/1982 | Jonell |
| 4,333,541 A | 6/1982 | Doty |
| 4,336,849 A | 6/1982 | Hug |
| 4,356,734 A | 11/1982 | Ivancsics |
| 4,482,021 A | 11/1984 | Repski |
| 4,828,047 A | 5/1989 | Rogerson |
| 4,869,115 A | 9/1989 | Edwards et al. |
| 4,989,678 A | 2/1991 | Thompson |
| 5,076,372 A | 12/1991 | Hellbusch |
| 5,211,248 A | 5/1993 | Nosewicz et al. |
| 5,213,169 A | 5/1993 | Heller |
| 5,394,949 A | 3/1995 | Wright et al. |
| 5,435,399 A | 7/1995 | Peterson et al. |
| 5,517,774 A | 5/1996 | Rogers |
| 5,741,983 A | 4/1998 | Skotnikov et al. |
| 5,887,491 A | 3/1999 | Monson et al. |
| 5,950,741 A | 9/1999 | Wright et al. |
| 5,991,687 A | 11/1999 | Hale et al. |
| 6,016,713 A | 1/2000 | Hale |
| 6,119,531 A | 9/2000 | Wendte et al. |
| 6,237,429 B1 | 5/2001 | Melnyk |
| 6,260,633 B1 | 7/2001 | Machek et al. |
| 6,360,829 B1 | 3/2002 | Naber et al. |
| 6,363,803 B1 | 4/2002 | Hubers |
| 6,484,654 B2 | 11/2002 | Chiu |
| 6,766,865 B1 | 7/2004 | Dagel et al. |
| 6,959,245 B2 | 10/2005 | Rooney et al. |
| 7,255,016 B2 | 8/2007 | Burton |
| 7,380,615 B1 | 6/2008 | Vanearden |
| 7,552,654 B2 | 6/2009 | Burton |
| 7,827,873 B2 | 11/2010 | Burton |
| 7,836,972 B2 | 11/2010 | Pavlik |
| 8,459,131 B2 | 6/2013 | Anderson |
| 8,613,234 B1 | 12/2013 | Harrell |
| 8,955,401 B1 | 2/2015 | Burton |
| 2005/0172733 A1 | 8/2005 | Drummond et al. |
| 2009/0178854 A1 | 7/2009 | Pavlik |
| 2011/0314938 A1 | 12/2011 | Anderson |
| 2012/0234934 A1 | 9/2012 | Score et al. |
| 2013/0319763 A1 | 12/2013 | McGraw |

SOIL SAMPLING ASSEMBLY

CROSS-REFERENCE TO RELATED APPLICATIONS

The present application is a continuation under 35 U.S.C. § 120 of U.S. patent application Ser. No. 14/486,058, filed Sep. 15, 2014, and titled "SOIL SAMPLING ASSEMBLY," which claims the benefit under 35 U.S.C. § 119(e) of U.S. Provisional Application Ser. No. 61/877,507, filed Sep. 13, 2013, and titled "SOIL SAMPLING ASSEMBLY," each of which is herein incorporated by reference in its entirety.

BACKGROUND

Soil samples collected from an agricultural field can be tested for relative nutrient status. This analysis can be used to more effectively direct the application of fertilizer to the field. In some instances, samples are taken from different regions within an agricultural field, and the application of fertilizer is varied with respect to the regions based upon relative differences in nutrient status, and so forth.

SUMMARY

A soil sampler assembly includes a utility vehicle and a soil sampler module coupled to the utility vehicle. The utility vehicle includes a cab, and the soil sampler module is configured to deposit a soil sample in the cab. For example, the soil sampler assembly includes a conveyor system configured to convey the soil sample to the cab. The conveyor system includes a central conveyor and a lateral conveyor that feeds the central conveyor. The central conveyor is on a travel track. The soil sampler assembly further includes a sampler arm assembly. The sampler arm assembly includes a power cylinder, a guide cylinder, a transfer block, and a probe. The probe has a tip, and the tip of the probe includes an outer surface defining an outer taper bore and an inner surface defining an inner taper bore.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items. Any dimensions included in the accompanying figures are provided by way of example only and are not meant to be restrictive of the present disclosure.

Figure 1:
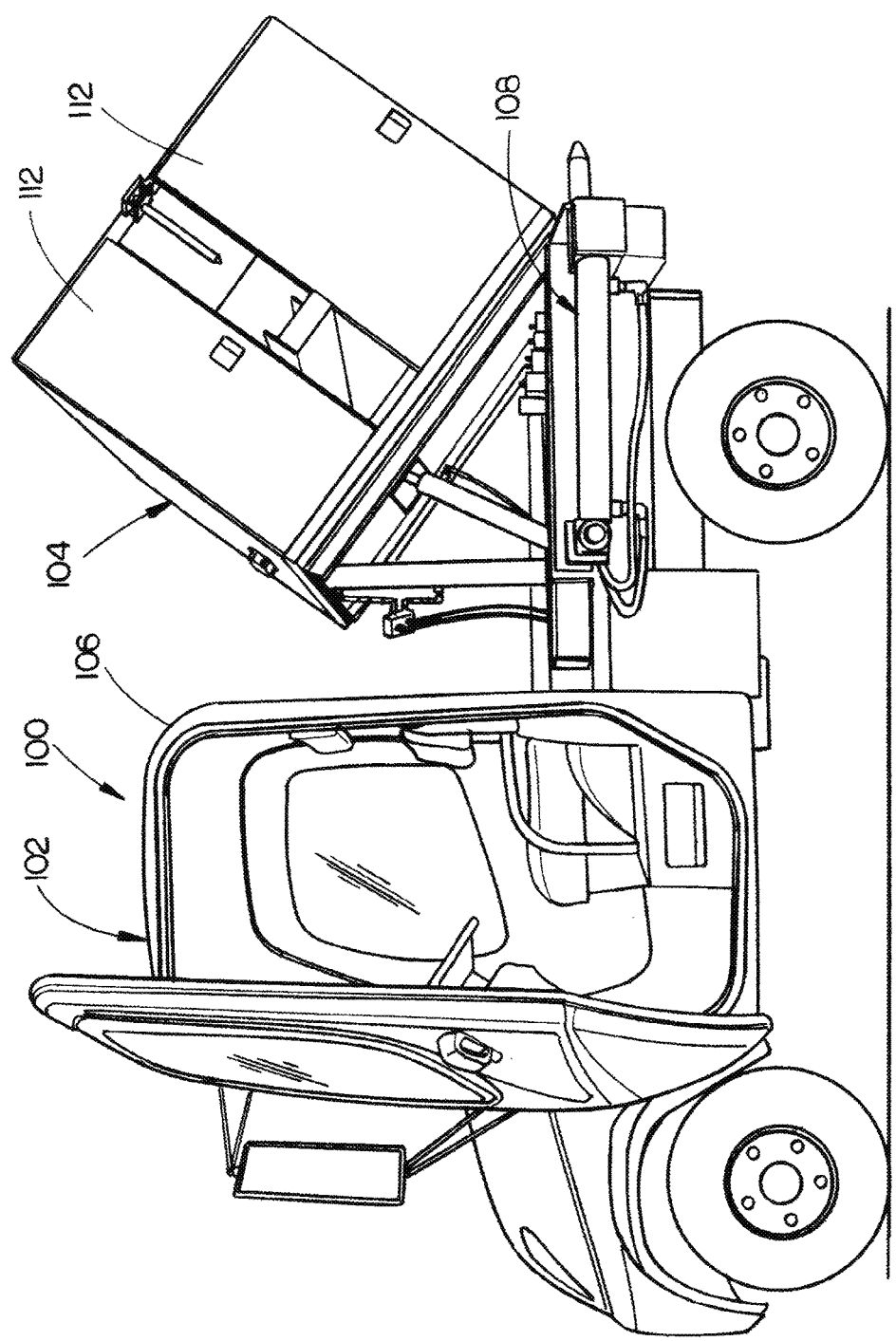
FIG. 1 is a left side elevation view of a soil sampler assembly including a utility vehicle and a soil sampler module, where the soil sampler module is tilted away from a cab of the utility vehicle in accordance with an example embodiment of the present disclosure.
Figure 2:
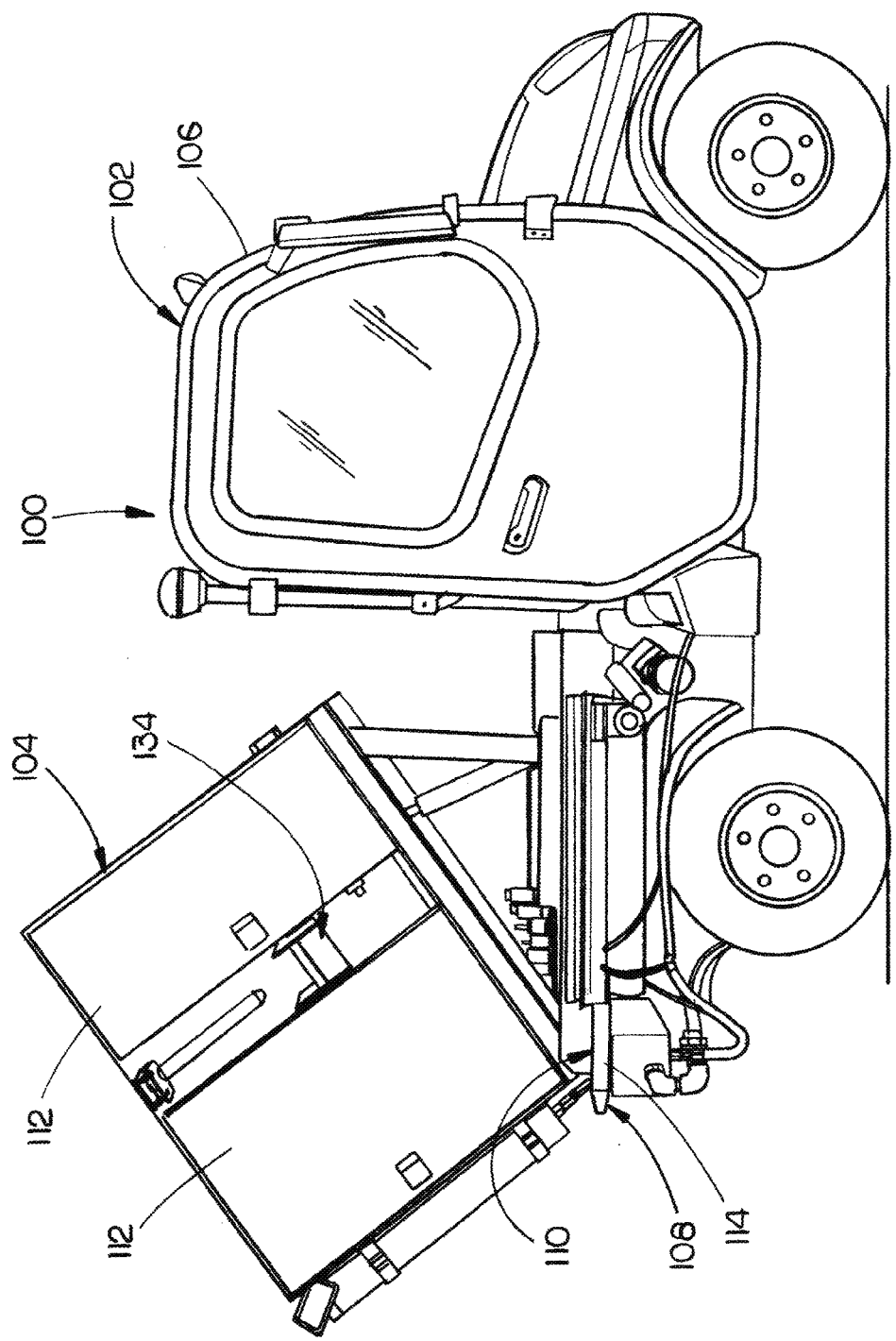
FIG. 2 is a right side elevation view of the soil sampler assembly illustrated in FIG. 1.
Figure 3:
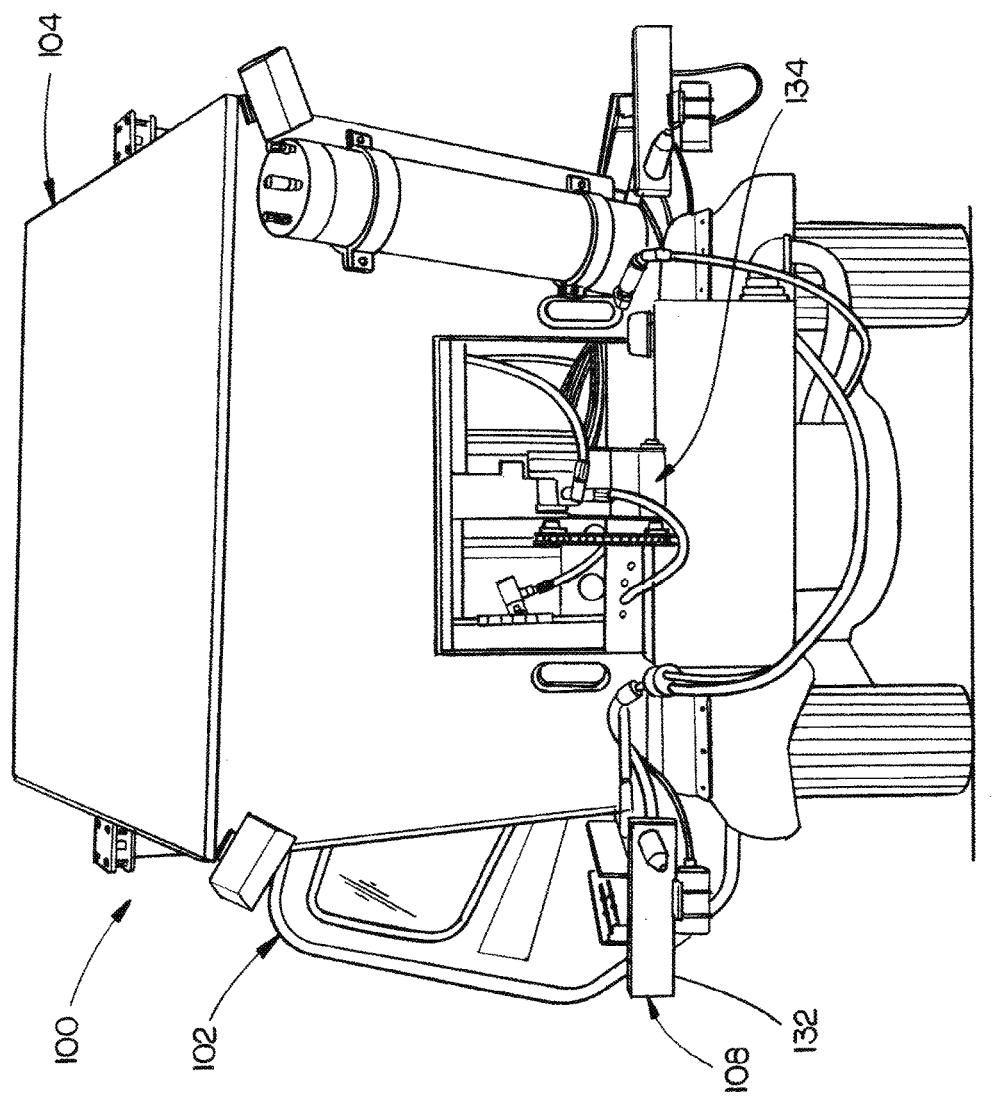
FIG. 3 is an end elevation view of the soil sampler assembly illustrated in FIG. 1.
Figure 4:
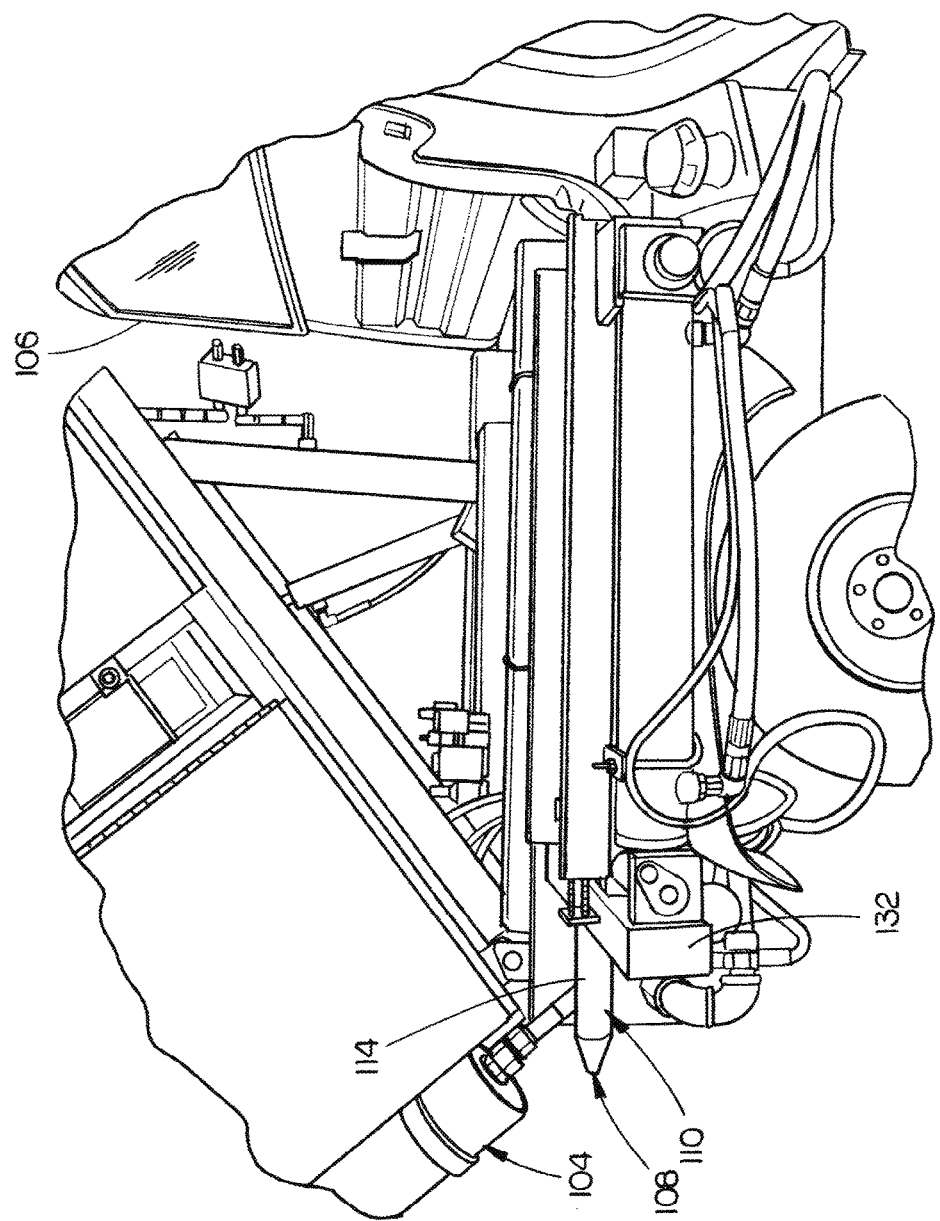
FIG. 4 is a partial right side elevation view of the soil sampler assembly illustrated in FIG. 1.
Figure 5:
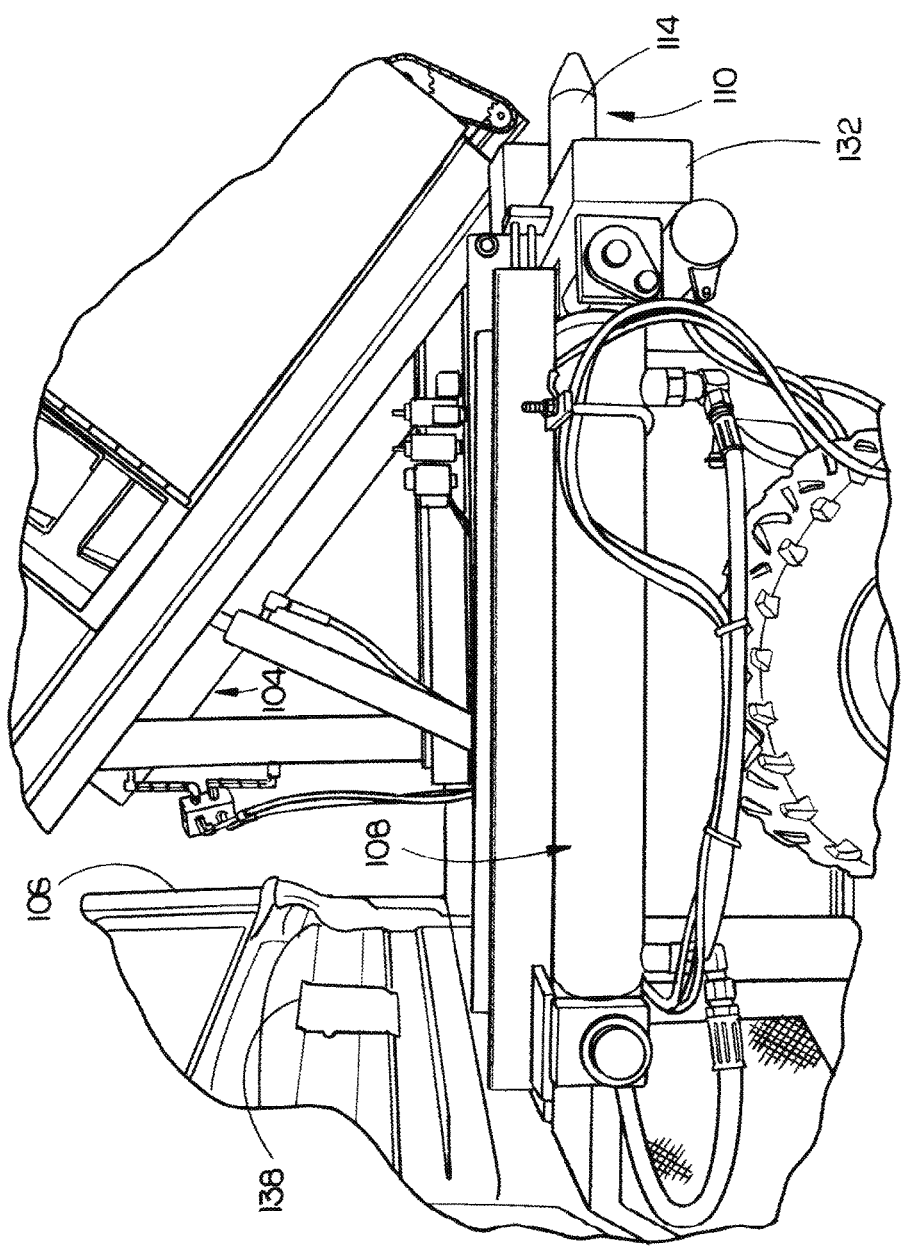
FIG. 5 is a partial left side elevation view of the soil sampler assembly illustrated in FIG. 1.
Figure 6:
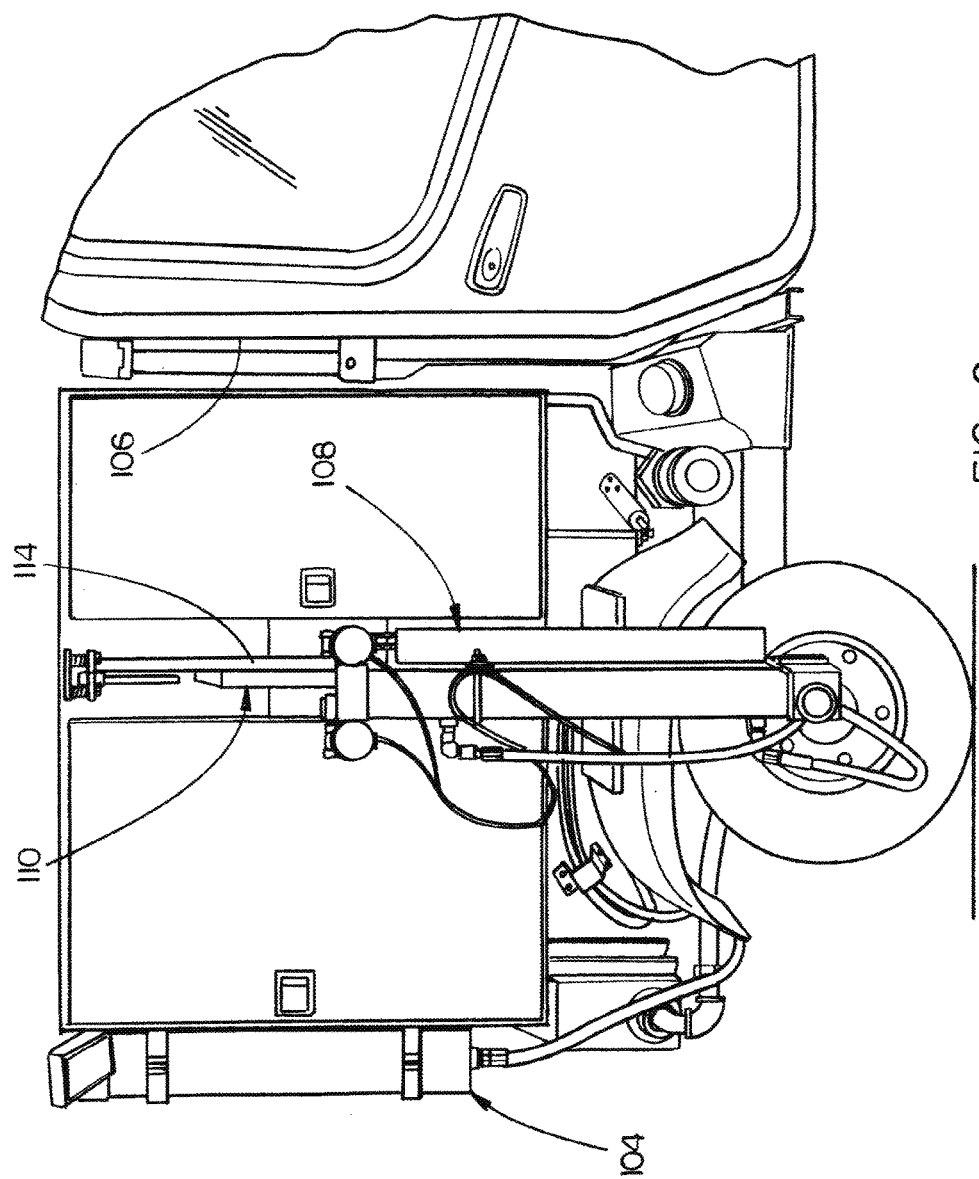
FIG. 6 is a partial right side elevation view of the soil sampler assembly illustrated in FIG. 1, where the soil sampler module is tilted toward the cab of the utility vehicle in accordance with example embodiments of the present disclosure.
Figure 7:
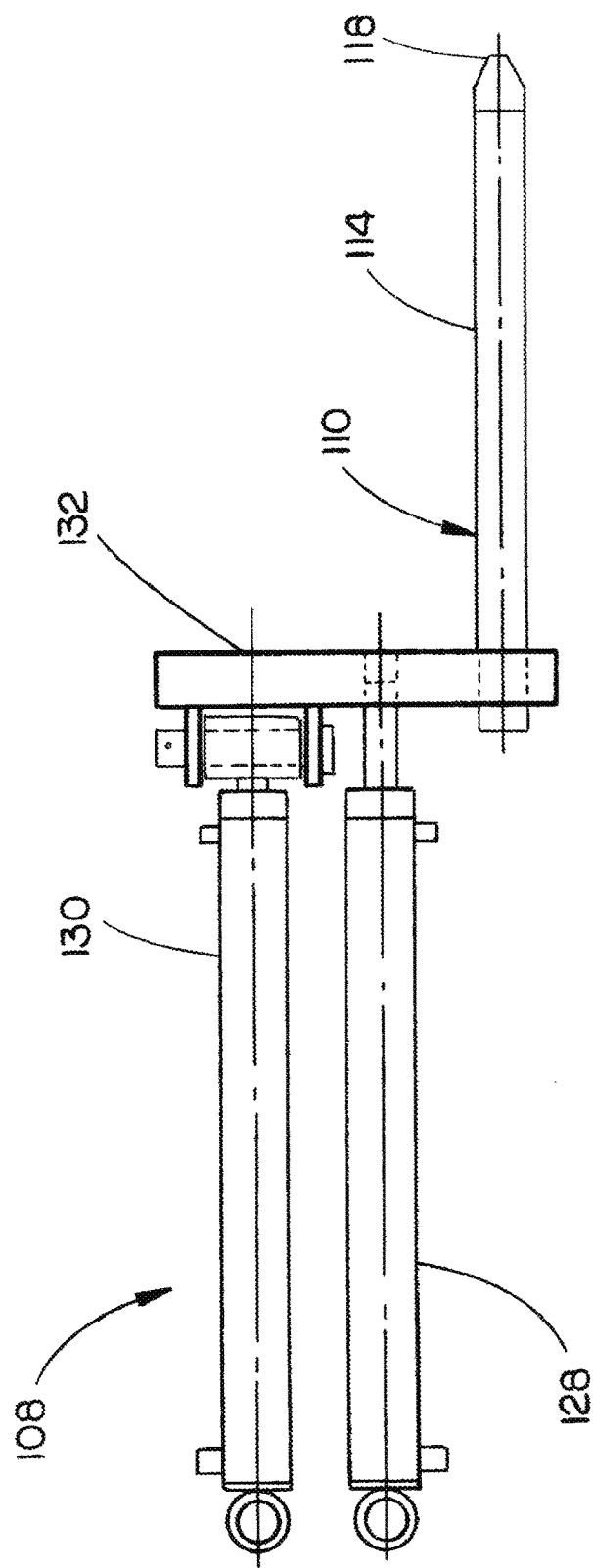
FIG. 7 is a schematic illustrating a sampler arm assembly for a soil sampler assembly, such as the soil sampler assembly illustrated in FIG. 1, in accordance with example embodiments of the present disclosure.
Figure 8:
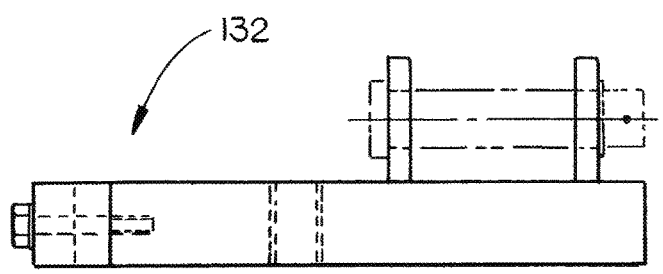
FIG. 8 is a side elevation view of a transfer block for a sampler arm assembly, such as the sampler arm assembly illustrated in FIG. 7, in accordance with example embodiments of the present disclosure.
Figure 9:
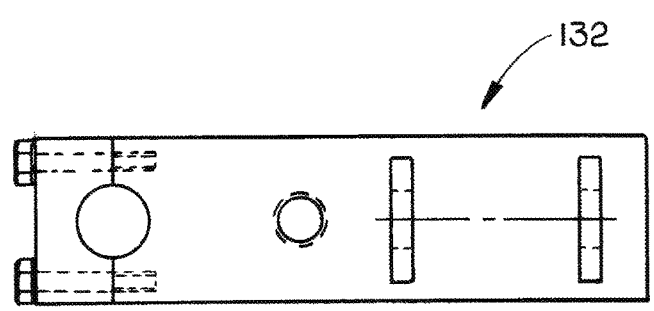
FIG. 9 is a top plan view of the transfer block illustrated in FIG. 8.
Figure 10:
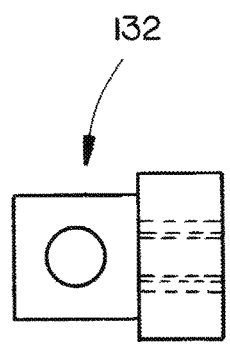
FIG. 10 is an end elevation view of the transfer block illustrated in FIG. 8.
Figure 11:
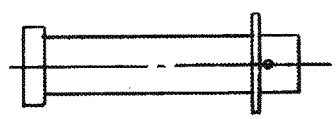
FIG. 11 is a side elevation view of a pin for coupling a guide cylinder to a transfer block, such as the transfer block illustrated in FIG. 8, in accordance with example embodiments of the present disclosure.
Figure 12:
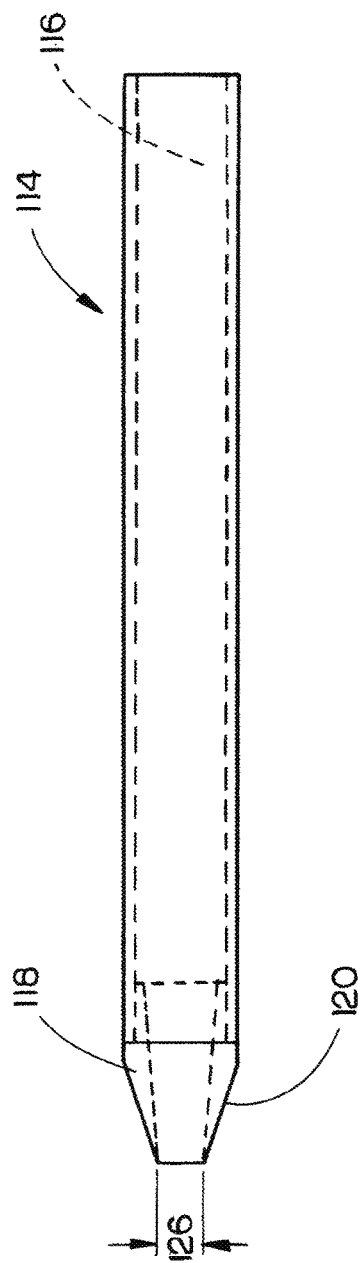
FIG. 12 is a side elevation view of a probe for a sampler arm assembly, such as the sampler arm assembly illustrated in FIG. 7, in accordance with example embodiments of the present disclosure.
Figure 13:
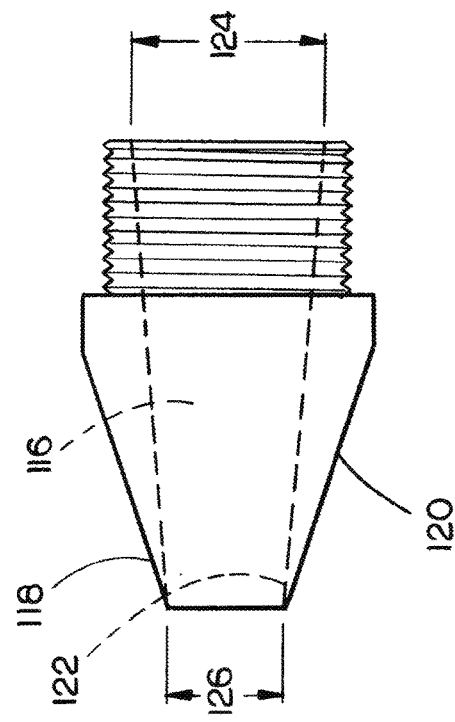
FIG. 13 is a side elevation view of a tip for a probe, such as the probe illustrated in FIG. 12, in accordance with example embodiments of the present disclosure.
Figure 14:
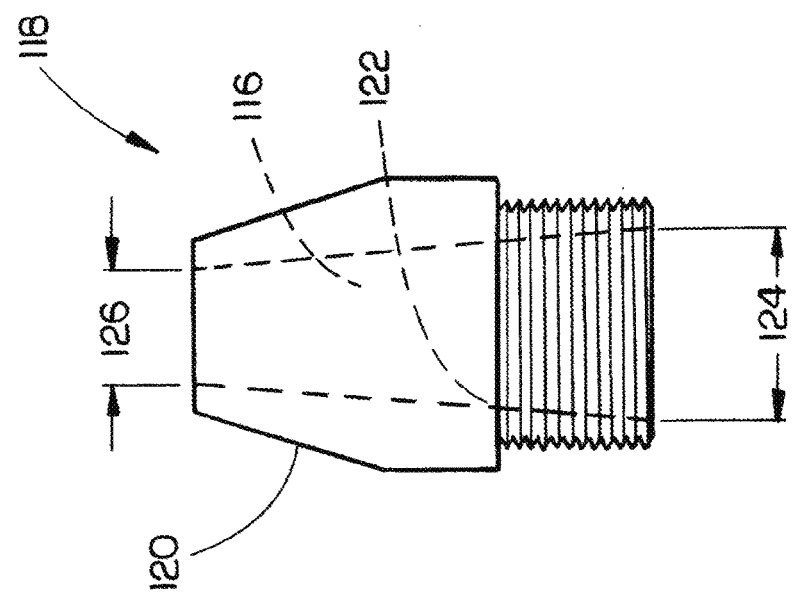
FIG. 14 is a side elevation view of another tip for a probe, such as the probe illustrated in FIG. 12, in accordance with example embodiments of the present disclosure.
Figure 15:
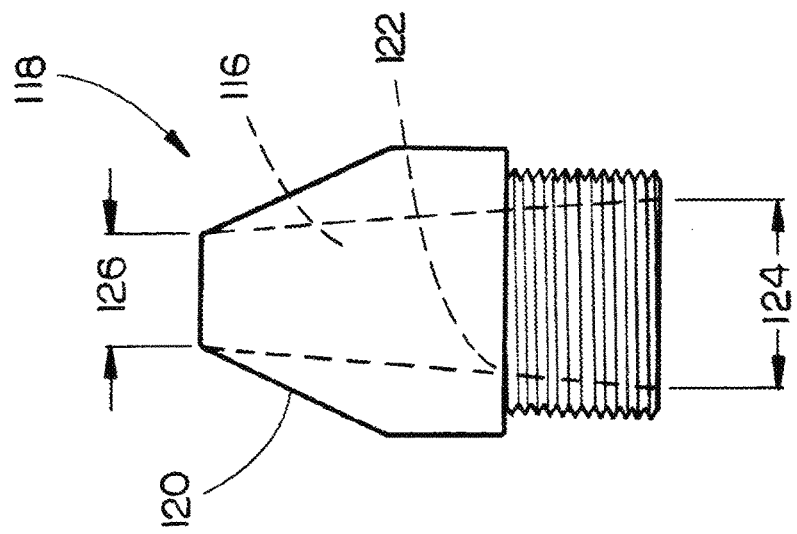
FIG. 15 is a side elevation view of yet another tip for a probe, such as the probe illustrated in FIG. 12, in accordance with example embodiments of the present disclosure.
Figure 16:
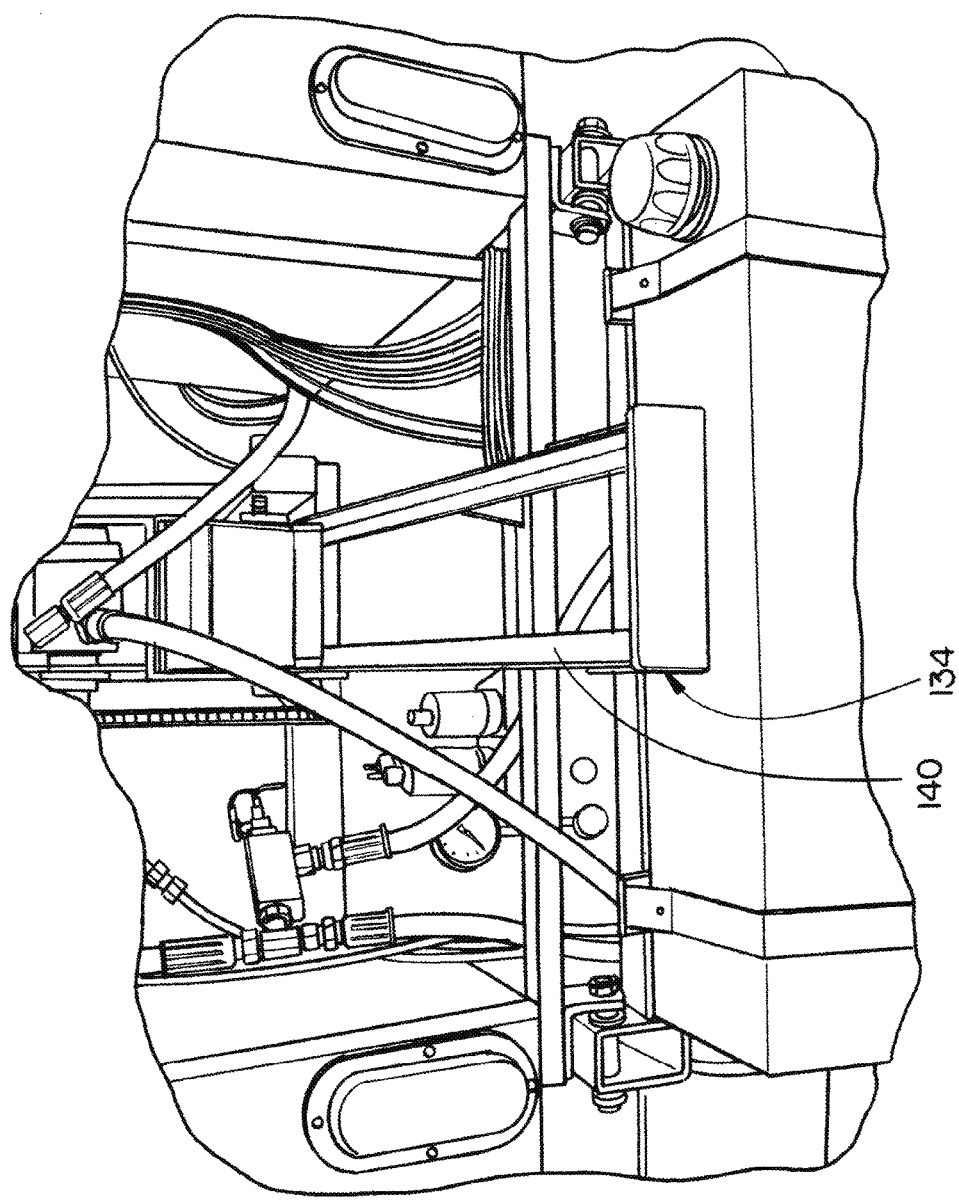
FIG. 16 is a partial end elevation view of the soil sampler assembly illustrated in FIG. 1, further illustrating a travel track for retracting a central conveyor belt from the cab of the utility vehicle.
Figure 17:
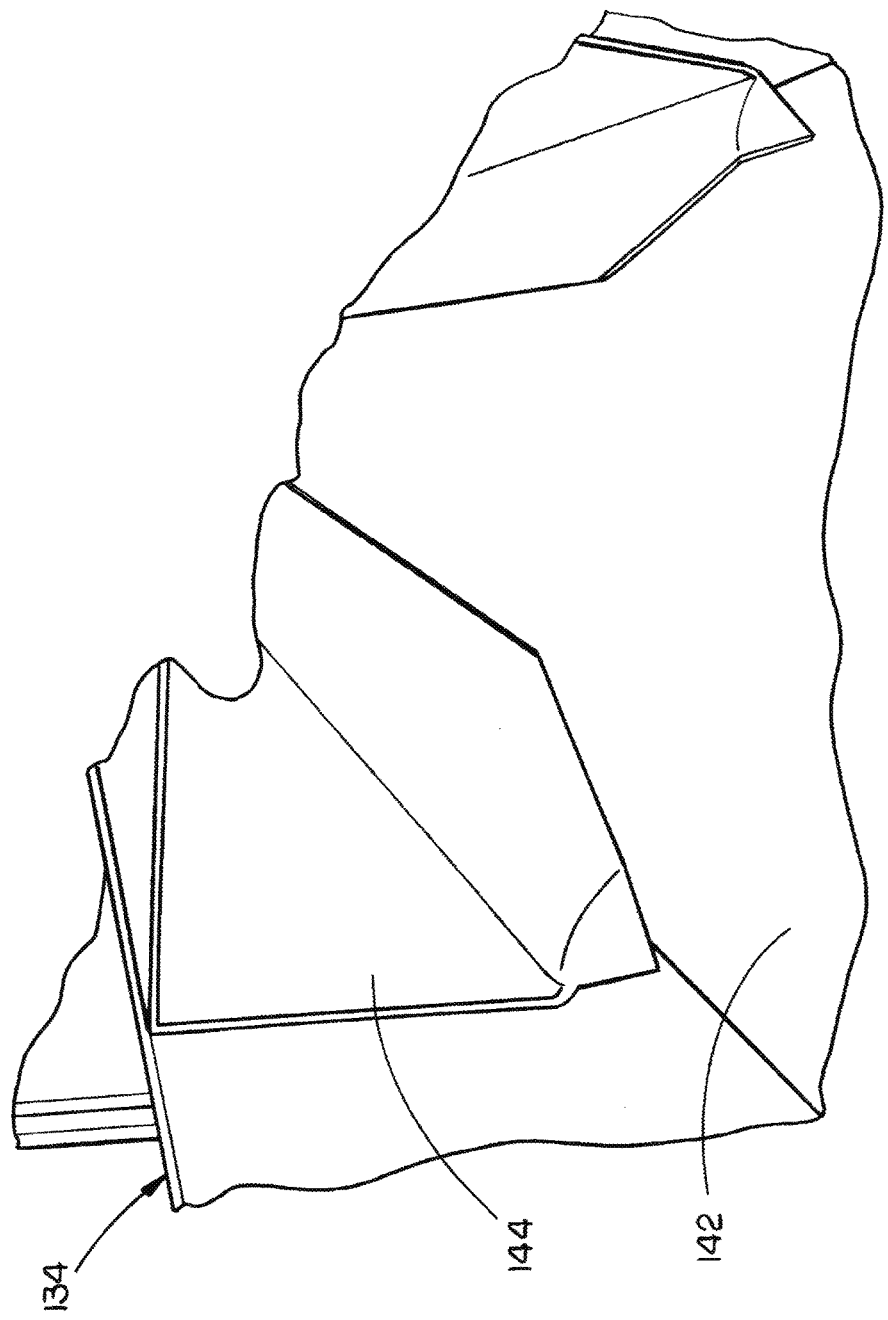
FIG. 17 is a partial perspective view of the soil sampler assembly illustrated in FIG. 1, further illustrating a lateral conveyor belt and guides for guiding cores along the lateral conveyor belt.
Figure 18:
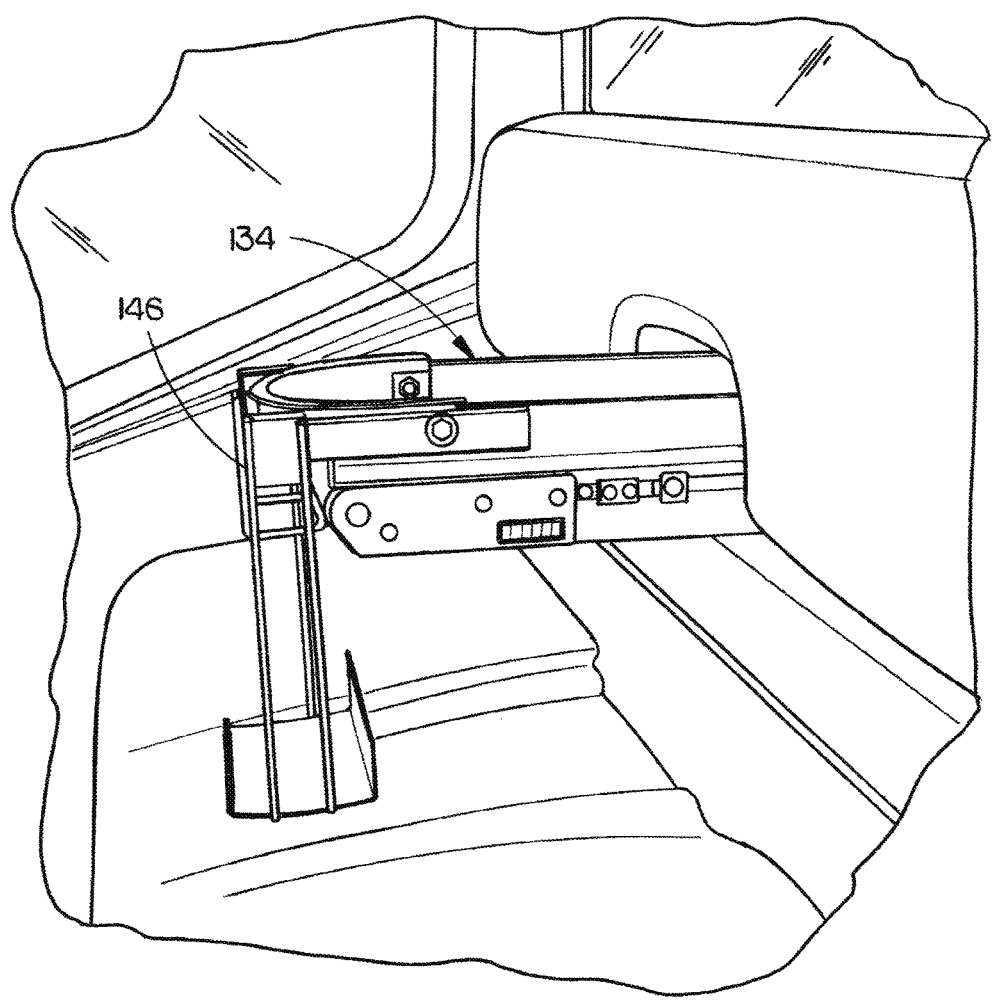
FIG. 18 is an interior view of the cab of the soil sampler assembly illustrated in FIG. 1, further illustrating a bag transition for collecting cores from the soil sampler module.
Figure 19:
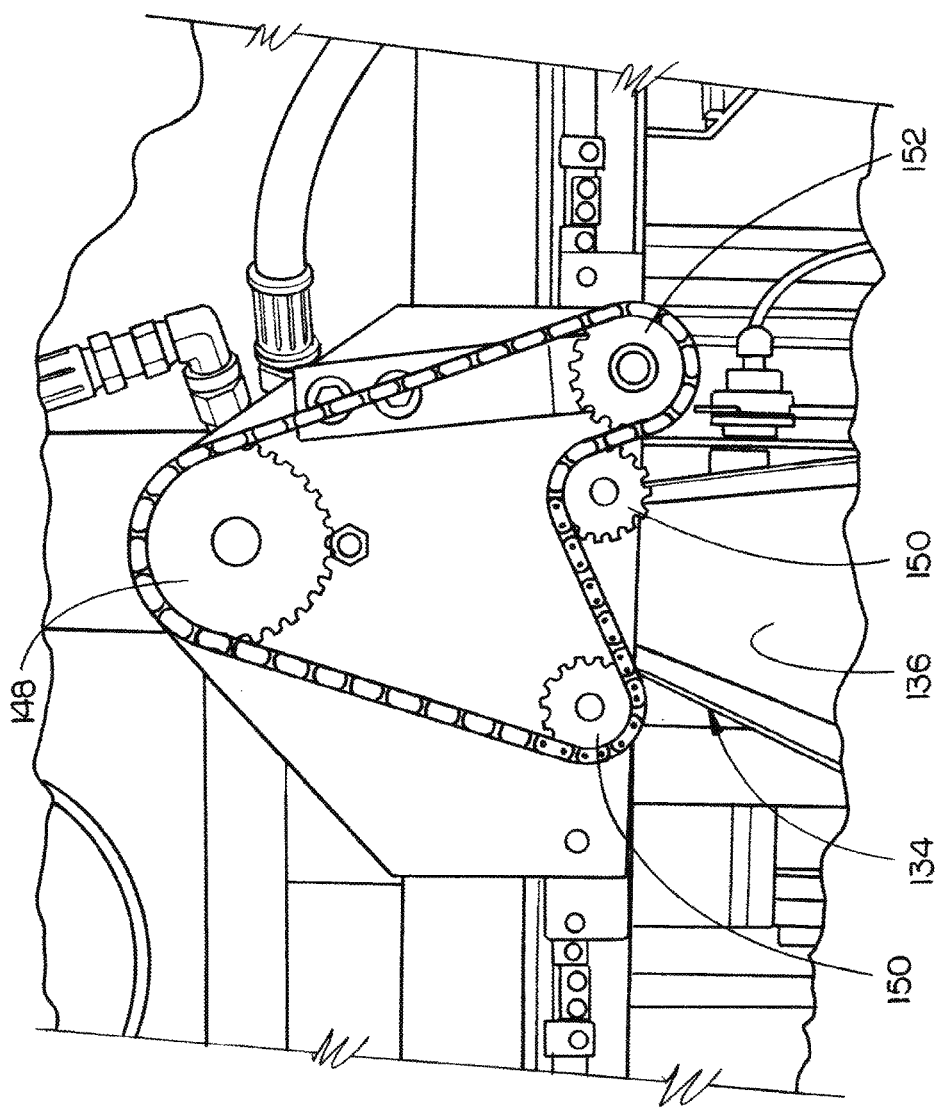
FIG. 19 is a partial end elevation view of the soil sampler assembly illustrated in FIG. 1, further illustrating a drive sprocket and power sprockets for driving the lateral conveyor belts of the soil sampler module.
Figure 20:
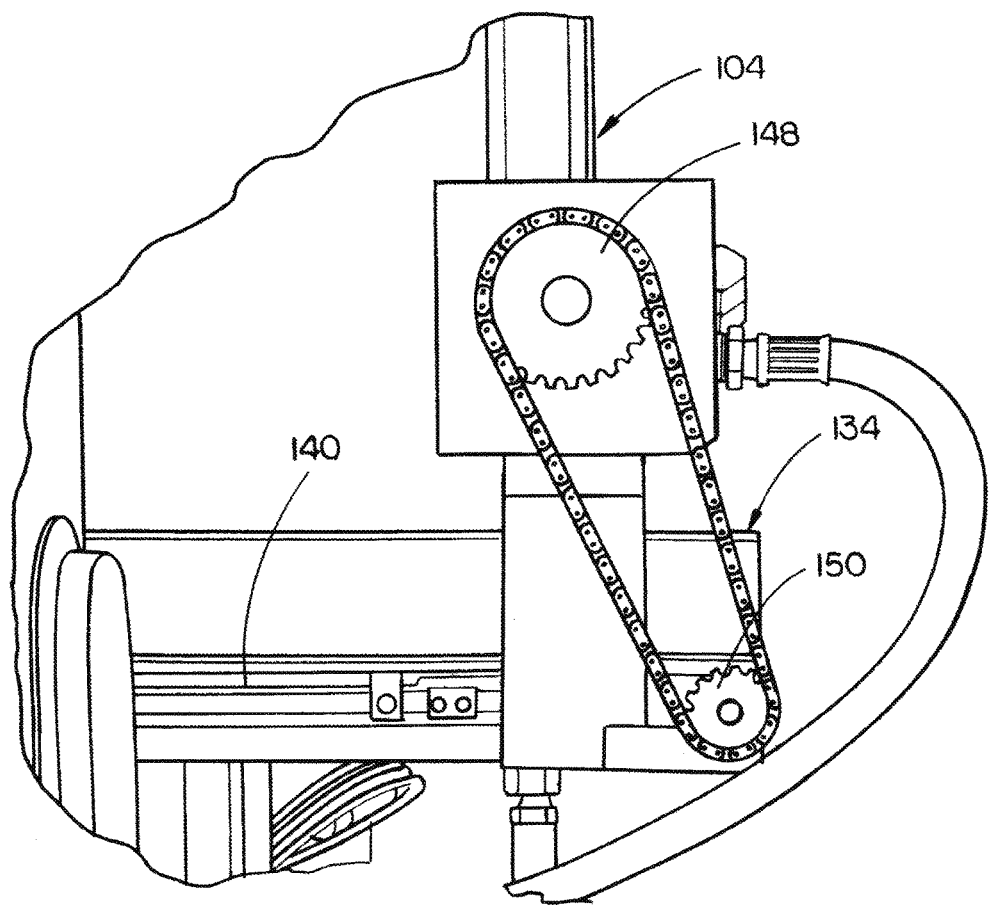
FIG. 20 is a partial side elevation view of the soil sampler assembly illustrated in FIG. 1, further illustrating another drive sprocket and another power sprocket for driving the central conveyor belt of the soil sampler module.
Figure 21:
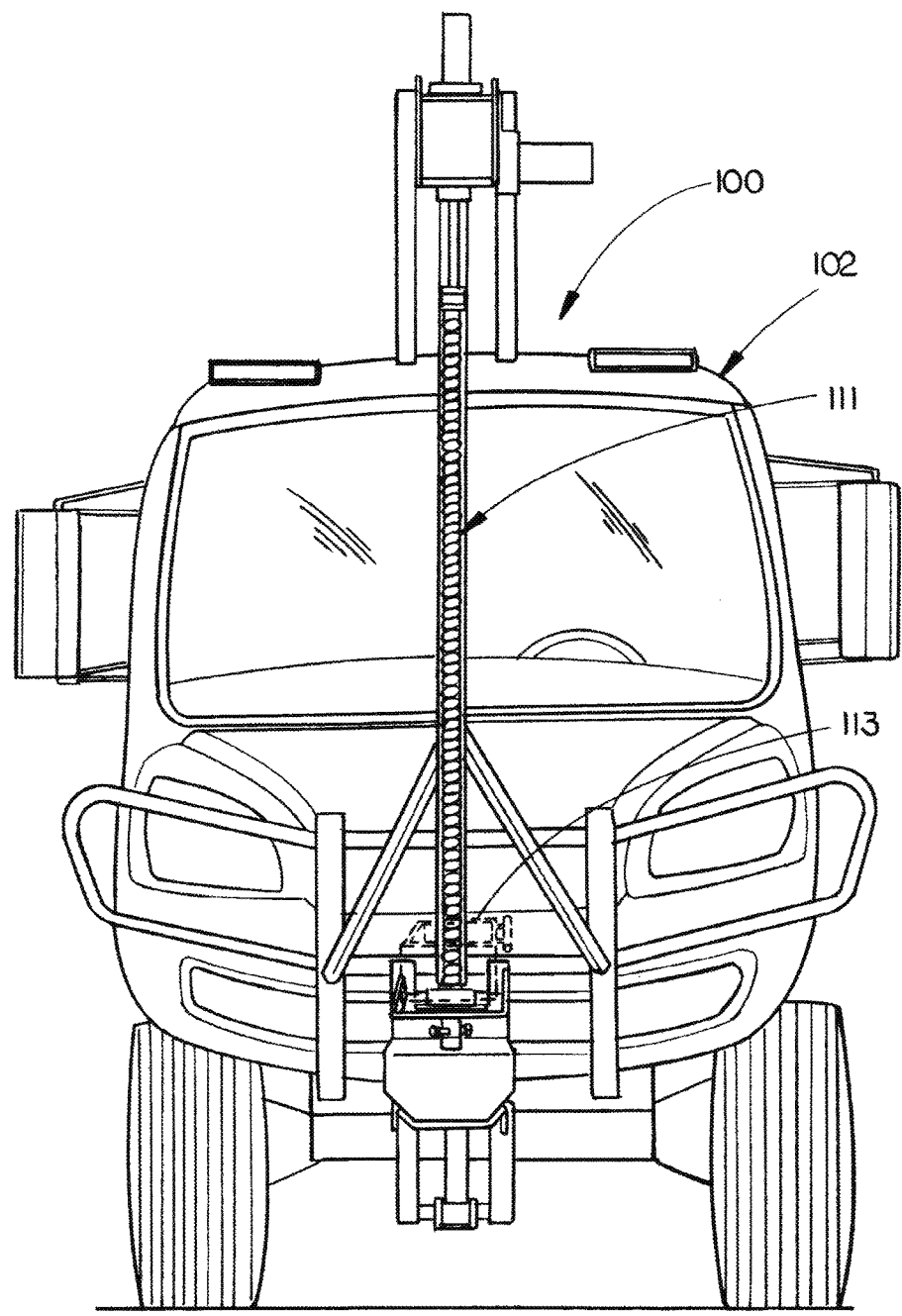
FIG. 21 is a front elevation view of a soil sampler assembly including a deep drill in accordance with an example embodiment of the present disclosure.
Figure 22:
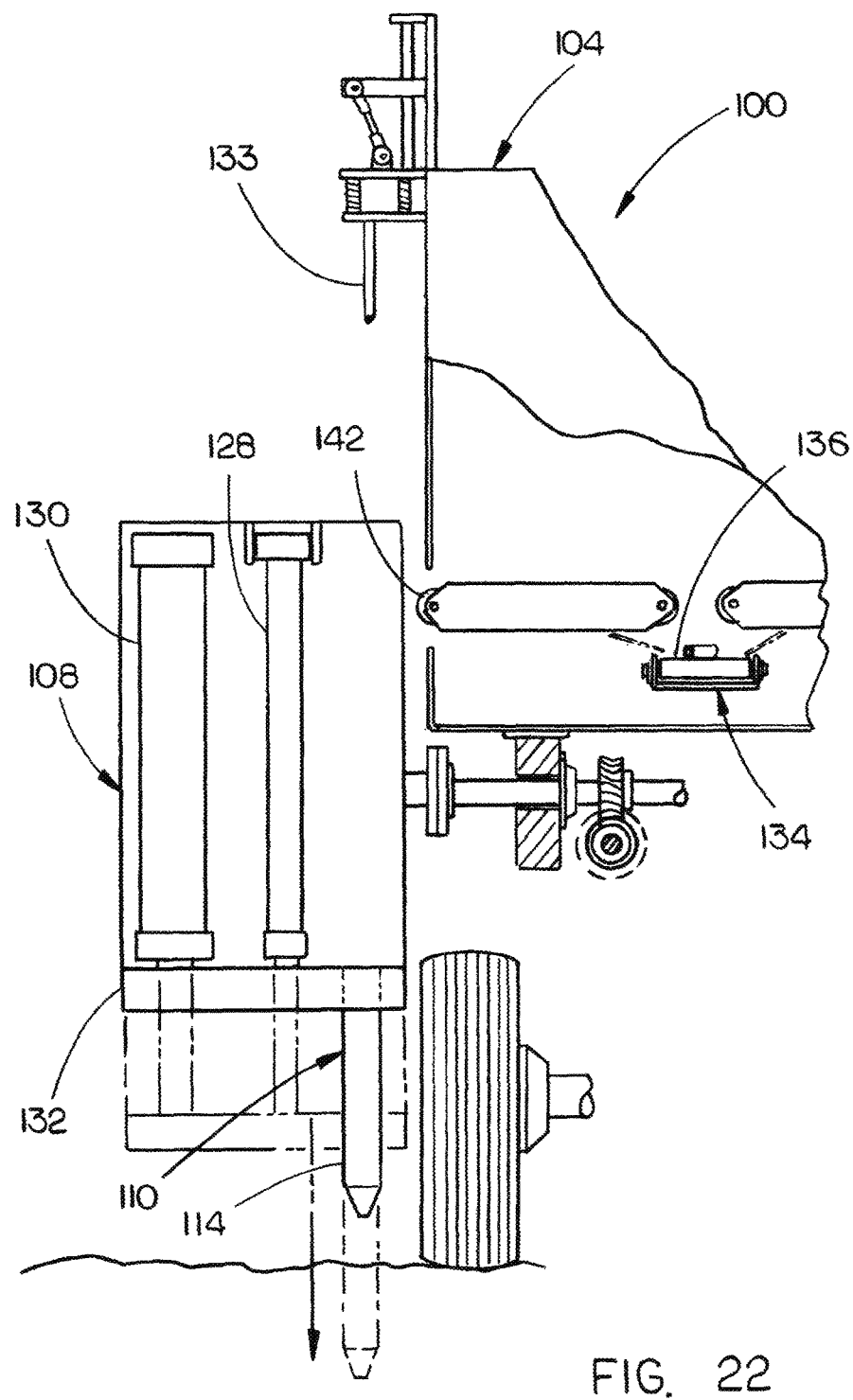
FIG. 22 is a partial end elevation view of the soil sampler assembly illustrated in FIG. 1, where a side drill including a probe is operated to enter the soil and obtain a sample of the soil in the form of a core in accordance with an example embodiment of the present disclosure.
Figure 23:
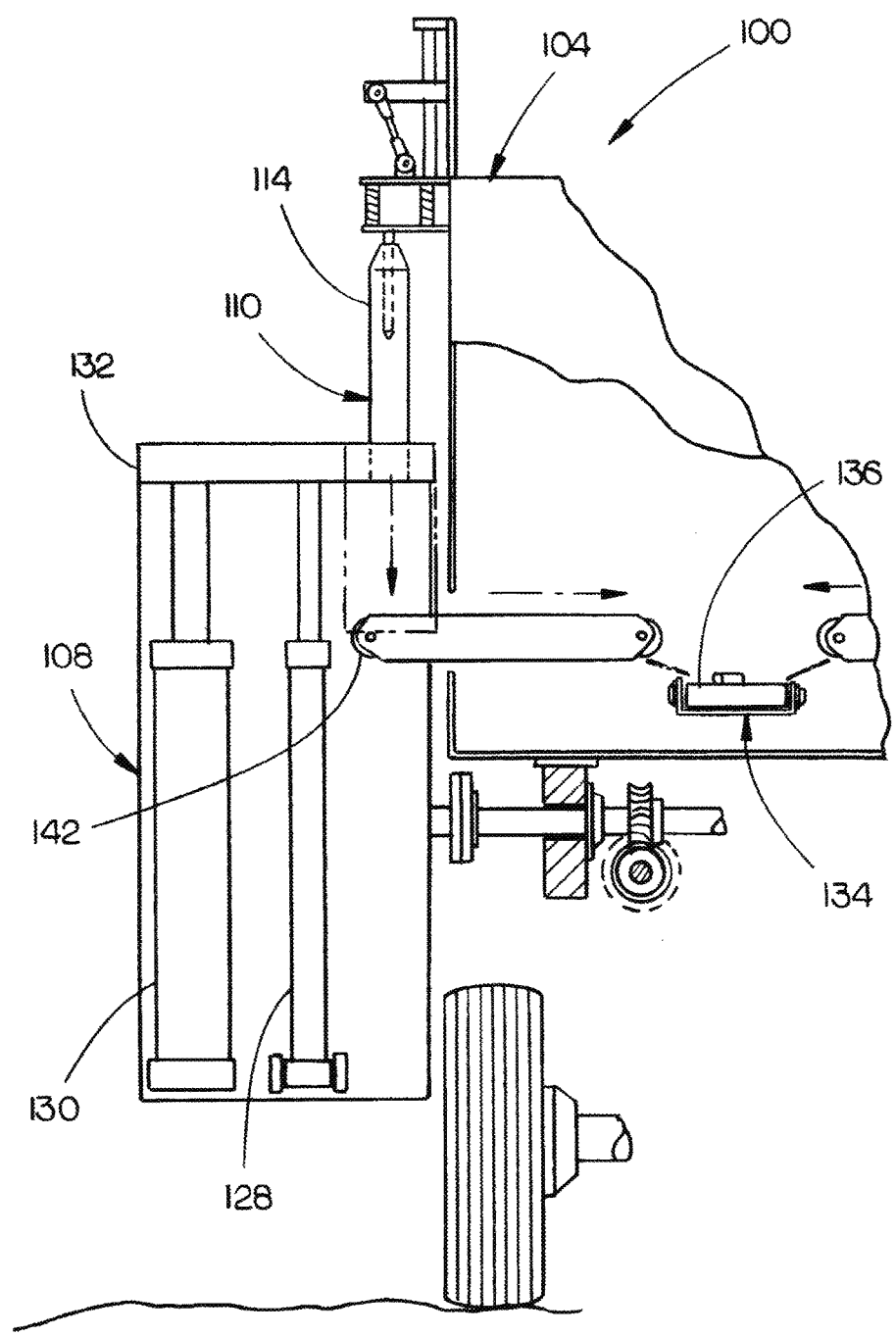

FIG. 23 is a partial end elevation view of the soil sampler assembly illustrated in FIG. 1, where the side drill is operable to rotate the probe from one vertical orientation facing the ground to another vertical orientation opposite the ground, and where the side drill is operated to release the core from the probe onto a lateral conveyor belt in accordance with an example embodiment of the present disclosure.

Figure 24:
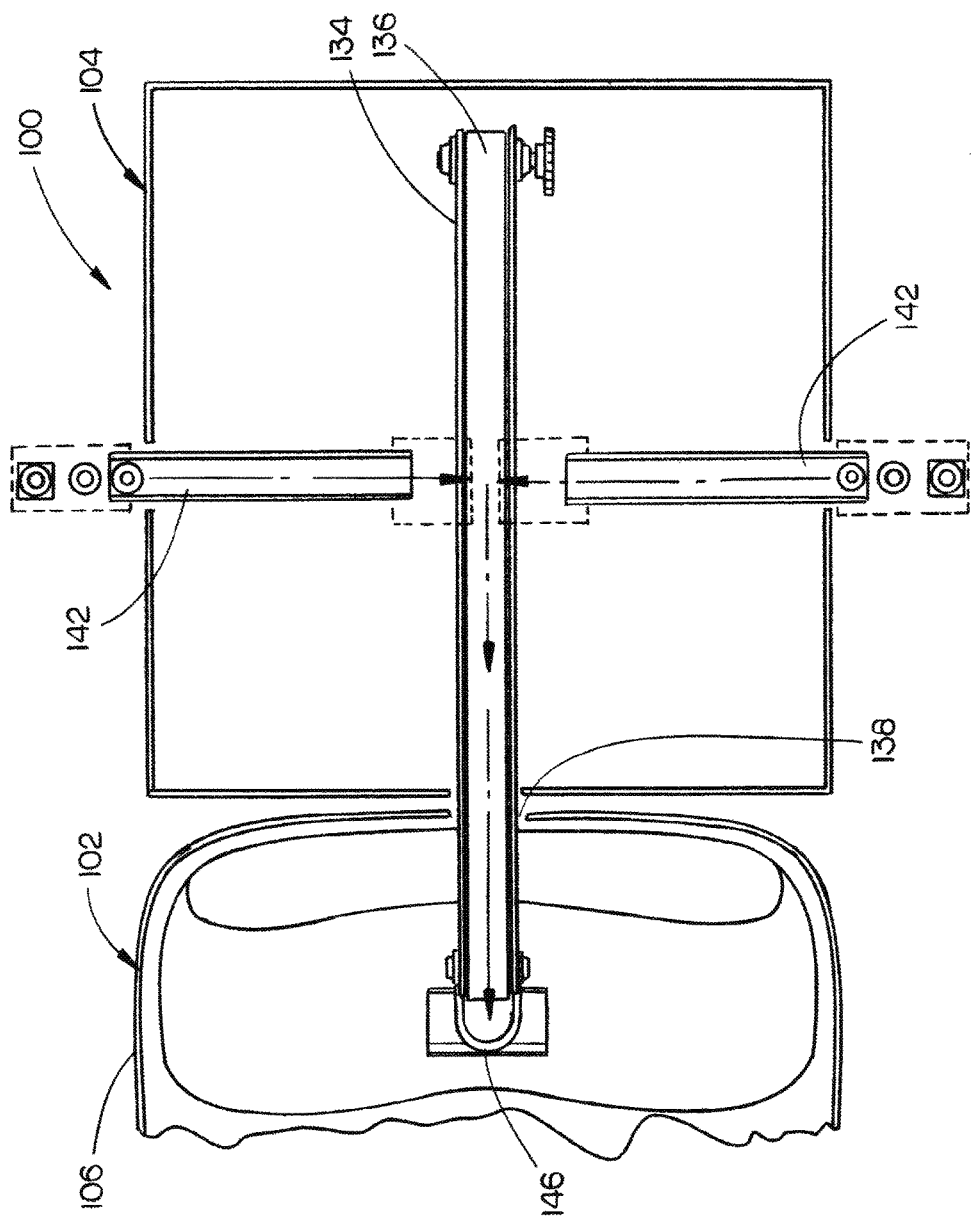

FIG. 24 is a partial top plan view of the soil sampler illustrated in FIG. 1, further illustrating a conveyor system including the central conveyor belt and two lateral conveyor belts in accordance with an example embodiment of the present disclosure.

DETAILED DESCRIPTION

Referring generally to FIGS. 1 through 24, a soil sampler assembly 100 is described. The soil sampler assembly 100 includes a utility vehicle 102 (e.g., an all-terrain vehicle (ATV), a utility task vehicle (UTV), and so forth) configured to support a soil sampler module 104. The soil sampler assembly 100 can be operated by a single operator. Further, the soil sampler assembly 100 can be used for low light (e.g., night) operations. In embodiments of the disclosure, soil testing performed with the soil sampler assembly 100 meets national soil testing requirements, university requirements, regulatory requirements, and so forth. In some embodiments, the soil sampler assembly 100 implements a "one-switch" complete sampling cycle, where a single switch is operated to initiate collection of one or more soil samples, which are received in the cab 106 of the utility vehicle 102.

The soil sampler module 104 supports one or more sampler arm assemblies 108. In some embodiments, the utility vehicle 102 also supports one or more sampler arm assemblies 108. For example, in some embodiments a sampler arm assembly 108 comprising a side drill 110 is included on each side of the soil sampler module 104, and a sampler arm assembly 108 comprising a deep drill 111 is included at the front of the utility vehicle 102. The side drills 110 and/or the deep drill 111 are operable to collect soil samples (e.g., cores/plugs) at various depths. For instance, soil samples are collected by the deep drill 111 at depths ranging from about four inches (4 in.) to about thirty-six inches (36 in.), at about two-inch (2 in.) intervals. In some embodiments, the side drills 110 are used to collect soil samples at five (5) different depths (e.g., at about two-inch (2 in.) intervals), and the deep drill 111 is used to collect soil samples at twelve (12) different depths (e.g., at about two-inch (2 in.) intervals). However, these ranges and intervals are provided by way of example only and are not meant to limit the present disclosure. In other embodiments, soil samples are collected at different depths, different intervals, and so forth. Further, sampler arm assemblies 108 can be positioned at different locations with respect to the utility vehicle 102 and/or the soil sampler module 104. For example, a sampler arm assembly 108 comprising a deep drill can be positioned at the rear of the utility vehicle 102.

In some embodiments, the deep drill 111 comprises a variable speed, fully reversible, rotary action drill mounted to the front of the utility vehicle 102. In some embodiments, the deep drill 111 is hydraulically powered. For example, the deep drill 111 can be hydraulically advanced and retracted. Further, a hydraulically powered deep drill 111 can be implemented as a variable speed drill, e.g., using one or more hydraulic check valves, which can be adjusted by an operator (e.g., using an adjustment tool, such as a hex key or wrench). The deep drill 111 is rotatable (e.g., rotating at least approximately ninety degrees) (90°) from a horizontal position to a vertical position). For example, the deep drill 111 is welded onto a hub that is rotatably secured to the front of the utility vehicle 102. The hub is used to lock the deep drill 111 in either the horizontal position or the vertical position using a spring-loaded lock pin, or the like. When the side drills 110 are used for high throughput sampling, the deep drill 111 can be locked in the horizontal orientation. Then, when sampling at deeper depths is desired, the lock pin is disengaged, the deep drill 111 is rotated to its vertical orientation, and the lock pin is reengaged.

In the vertical position, the bottom end of the deep drill 111 can be telescoped about twelve inches (12 in.) from the ground. This allows the utility vehicle 111 to be driven between successive sampling locations (e.g., over variable terrain). When a sample is acquired, the bottom end of the deep drill 111 is telescoped to ground level, the auger is used to obtain a core from the soil, and the bottom end of the deep drill 111 is then telescoped away from ground level. In some embodiments, the soil sampler assembly 100 includes a removable receiving pan 113. The receiving pan 113 can define an aperture through which the auger of the deep drill 111 extends. As the core is moved upwardly by the threads of the auger, the core is dropped into the receiving pan 113 for retrieval by the operator. In some embodiments, the receiving pan 113 includes one or more handles configured to enable the operator to remove the receiving pan 113 from the soil sampler assembly 100. In embodiments of the disclosure, telescoping and/or sampling operations are initiated by the operator from the cab 106 of the utility vehicle 102 (e.g., via a switch, a button, and so forth positioned in the cab 106).

In some embodiments, the utility vehicle 102 comprises a three-cylinder, four-cycle diesel engine with about sixty-eight and one-half cubic inches (68.5 cu. in.) of displacement. The engine of the utility vehicle 102 generates about twenty-four and eight-tenths horsepower (24.8 HP) at three thousand revolutions per minutes (3,000 rpm). The utility vehicle 102 has a maximum travelling speed of about twenty-five miles per hour (25 mph). The utility vehicle 102 is about one hundred twenty-nine and one-tenth inches (129.1 in.) long, sixty-six and nine-tenths inches (66.9 in.) wide, and eighty-one and one-half inches (81.5 in.) in height. The utility vehicle 102 weighs about two thousand four hundred and eighty pounds (2,480 lbs.). However, this configuration is provided by way of example only and is not meant to limit the present disclosure. In other embodiments, the utility vehicle 102 has a differently sized engine, a different maximum travelling speed, different overall dimensions, a different weight, and so forth.

The utility vehicle 102 is configured to support the soil sampler module 104, which is securely connected to, for instance, the rear of the utility vehicle 102. In some embodiments, the soil sampler module 104 can be efficiently disconnected from the utility vehicle 102. For example, U-bolt fasteners are used to connect the soil sampler module 104 to the utility vehicle 102 and can be easily disengaged to disconnect the soil sampler module 104 from the utility vehicle 102. In embodiments of the disclosure, the soil sampler module 104 can be tilted to provide access to portions of the utility vehicle 102 and/or the soil sampler module 104 that would not otherwise be accessible. For example, the soil sampler assembly 100 includes a linkage rotation system configured to tilt the soil sampler module 104 with respect to the utility vehicle 102. In other embodiments, the soil sampler assembly 100 includes a rack-and-pinion system to tilt the soil sampler module 104 with respect to the utility vehicle 102. In these configurations, the soil sampler assembly 100 uses, for instance, an electric over hydraulic system. In some embodiments, the soil sampler module 104 includes one or more utility boxes 112 configured for onboard storage. Further, the soil sampler module 104 has a louvered roof or the like to facilitate heat dissipation.

In embodiments of the disclosure, the soil sampler module 104 is powered by the engine of the utility vehicle 102. For example, the soil sampler assembly 100 implements a split pump system operated with one motor (e.g., the engine of the utility vehicle 102). In this configuration, a first hydraulic pump is used to tilt the soil sampler module 104 with respect to the utility vehicle 102, and a second hydraulic pump is used to operate the sampler arm assemblies 108. A hydraulic accumulator is also provided to store hydraulic energy. In some embodiments, the soil sampler assembly 100 includes a twelve gallon (12 gal.) oil reservoir, e.g., where one hydraulic pump is configured to pump at a rate of five gallons (5 gal.) per minute, and another hydraulic pump is configured to pump at a rate of seven gallons (7 gal.) per minute, for a combined rate of twelve gallons (12 gal.) per minute. A coupling can be used to couple the two hydraulic pumps together. One or more of the hydraulic pumps can be operated at a pressure of at least approximately two thousand pounds per square inch (2,000 psi). Further, the soil sampler assembly 100 can implement integrated cooling of the oil reservoir. However, this configuration is provided by way of example only and is not meant to limit the present disclosure. In other embodiments, different equipment is used to power the soil sampler module 104 and/or the sampler arm assemblies 108, such as electric motors, and so forth. In some embodiments, the soil sampler assembly 100 is configured with a split electrical function, where components of the soil sampler module 104 are separately fused from the ignition of the utility vehicle 102. In this manner, the soil sampler module 104 is not operated during road functions of the utility vehicle 102.

Each one of the side drills 110 includes a probe 114 configured to enter soil to a certain depth and obtain a sample of the soil in the form of a core. The probe 114 is generally longitudinal, defining an interior channel 116 configured to receive the core and subsequently release the core for collection. In some embodiments, the probe 114 is between about ten inches (10 in.) and about fourteen inches (14 in.) in length, tapering at a tip 118. An outer surface 120 of the tip 118 of the probe 114 comprises an outer taper bore, and an inner surface 122 of the tip 118 of the probe 114 comprises an inner taper bore. The taper extends about three inches (3 in.) in length, and the ratio of the inside diameter 124 of the inner surface 122 distal to the end of the tip 118 to the inside diameter 126 of the inner surface 122 proximal to the end of the tip 118 is about two-to-one (2:1). For example, the inside diameter 124 of the inner surface 122 distal to the end of the tip 118 is about one and one-half inches (1.5 in.), and the inside diameter 126 of the inner surface 122 proximal to the tip 118 of the probe 114 is about three-quarters of one inch (¾ in.). However, this ratio is provided by way of example only and is not meant to limit the present disclosure. In another embodiment, the ratio of the inside diameter 124 of the inner surface 122 distal to the end of the tip 118 to the inside diameter 126 of the inner surface 122 proximal to the end of the tip 118 is about one and two-thirds-to-one (1.67:1). For example, the inside diameter 124 of the inner surface 122 distal to the end of the tip 118 is about one and one-quarter inches (1.25 in.), and the inside diameter 126 of the inner surface 122 proximal to the tip 118 of the probe 114 is about three-quarters of one inch (¾ in.).

The probe 114 includes a trap door configured to retain a core when the probe 114 is inserted into the soil. As the probe 114 is inserted into the soil, the core is pushed through the interior channel 116 and past the trap door. Then, after the core is collected and the probe 114 of the side drill 110 is retracted from the soil, the trap door retains the core in the interior channel 116 of the probe 114. In some embodiments, the probe 114 is machined from a metal material (e.g., stainless steel), and the outer surface 120 and/or the inner surface 122 of the tip 118 of the probe 114 are surface finished (e.g., to a micro-machined finish). In this manner, the probe 114 may be used repeatedly without application of lubricant. Further, repeated use of the probe 114 may cause the outer surface 120 and/or the inner surface 122 of the tip 118 to become more polished over time, sharpening the tip 118. However, this configuration is provided by way of example only and is not meant to limit the present disclosure. In other embodiments, the probe 114 is fabricated from one or more different materials, possibly having different surface finishes. Further, in some embodiments, the probe 114 is used with the application of a lubricant.

Each sampler arm assembly 108 includes a mechanism for driving the probe 114 into the soil. For example, the sampler arm assembly 108 includes a power cylinder 128 configured to power longitudinal translation of the probe 114. In some embodiments, the power cylinder 128 is positioned coaxially with the probe 114. In other embodiments, the longitudinal axis of the power cylinder 128 is offset from the longitudinal axis of the probe 114. The sampler arm assembly 108 also includes a guide cylinder 130 configured to facilitate linear translation of the probe 114. In some embodiments, the longitudinal axis of the guide cylinder 130 is offset from the longitudinal axis of the probe 114, while in other embodiments the guide cylinder 130 is positioned coaxially with the probe 114. The power cylinder 128 and/or the guide cylinder 130 are coupled to the probe 114 via a transfer block 132. The transfer block 132 and the power cylinder 128 implement a vibrating hammer to facilitate collection of a core from the soil. For instance, as the power cylinder 128 is actuated to translate the probe 114 into the soil, the transfer block 132 vibrates the probe 114 to penetrate the soil and facilitate access by the probe 114. However, this configuration is provided by way of example only and is not meant to limit the present disclosure. In other embodiments, the sampler arm assembly 108 is powered using another type of drive. For example, the deep drill 111 is implemented using an auger extending through a collection pan (e.g., receiving pan 113). The auger lifts a soil sample up its flights and deposits the soil sample on the collection pan. In some embodiments, the collection pan is accessible from the cab 106 of the utility vehicle 102 (e.g., through an aperture defined proximate to the floor of the cab 106).

In embodiments of the disclosure, the soil sampler assembly 100 is configured to provide about two inches (2 in.) of air travel between the probe 114 and the soil. In some embodiments, the utility vehicle 102 is equipped with air shocks and/or air bags to adjust the height of the sampler arm assembly 108 with respect to the surface of the soil. Further, one or more of the sampler arm assemblies 108 includes a proximity switch configured to control the depth of the probe 114 as it enters the soil. The proximity switch can be used to ensure that an appropriate depth is reached in various soil conditions, including but not necessarily limited to: mud, sand, and so forth. In some embodiments, one or more backup switches are included to further limit translation of the probe 114, including one or more redundant proximity switches, one or more timed switches, and so forth. For instance, a timed switch can be used to control the depth of the probe 114 as it enters the soil (e.g., in place of a proximity switch, in addition to a proximity switch, and so forth). In some embodiments, when a proximity switch may become damaged or otherwise inoperable, a timer can be used to control the depth of the probe 114 as it enters the soil. In some embodiments, the timer can be set by an operator. In some embodiments, control algorithms can be used by the soil sampler assembly 100, e.g., automatically timing how long it takes the probe 114 to reach a particular depth, and then determining a characteristic (e.g., average) time to control subsequent timing for the depth of the probe 114. Such algorithms can also take into account different soil types for different geographic regions (e.g., determined using positioning measurements, such as global positioning system (GPS) measurements, and so forth).

After a core is collected and the probe 114 of the side drill 110 is retracted from the soil, the probe 114 is rotated about one hundred and eighty degrees) (180°) from a first vertical orientation facing the ground to a second vertical orientation opposite the ground. In this orientation, the core is released from the probe 114 onto one of the lateral conveyor belts 142 as described. As noted, the inner taper bore of the tip 118 of the probe 114 facilitates removal of the core from the probe 114 via gravity. In some embodiments, a brush is positioned proximate to the tip 118 of the probe 114 when the probe 114 is oriented in the second vertical orientation opposite the ground. In this orientation, the brush is extended into the tip 118 of the probe 114 to clean the probe 114 between successive soil samples. However, it should be noted that the action of the brush may serve to clean the tip 118 of the probe 114 and not necessarily to remove the core from the probe. In this manner, cross-contamination between samples can be minimized or prevented.

In some embodiments, the soil sampler assembly 100 includes an eject sensor (e.g., a knockout peg) to determine whether the probe 114 has become plugged with soil and/or one or more other materials. For example, the soil sampler assembly 100 can be equipped with a self-resetting knockout peg assembly. In some embodiments, a knockout peg comprising a shaft 133 extends downwardly from proximate to the top of the soil sampler assembly 100. When the probe 114 is rotated from the first vertical orientation facing the ground to the second vertical orientation opposite the ground, the probe 114 can be extended to receive the shaft 133. When a soil sample has been properly ejected from the probe 114, the shaft 133 may not be contacted. However, when the shaft 133 contacts a soil sample lodged in the probe 114, a sensor (e.g., a linear actuation sensor, a contact sensor, or another sensor) can be used to alert the operator that the probe 114 has become plugged. In some embodiments, the sensor can be coupled with a switch that limits and/or removes power from the sampler arm assembly 108 and/or one or more other subsystems or components of the soil sampler assembly 100. The switch can implement self-resetting functionality. For instance, a reset mechanism for the switch can require the operator to exit the cab 106 of the utility vehicle 102 to perform a reset operation. In some embodiments, a reset mechanism can be provided in the cab 106 of the utility vehicle 102. In this manner, the operator can be alerted to a clogged probe condition, and may be required to perform a maintenance operation and/or a visual inspection before operation of the soil sampler assembly 100 can resume.

The soil sampler assembly 100 has a conveyor system 134 configured to move cores from the side drill 110 to the cab 106 of the utility vehicle 102 for in-bag, in-cab collection. In embodiments of the disclosure, a central conveyor belt 136 extends longitudinally through the soil sampler module 104 and into the cab 106 of the utility vehicle 102 (e.g., via an aperture 138 defined in the cab 106). The central conveyor belt 136 is on a travel track 140, allowing the central conveyor belt 136 to be retracted from the cab 106 of the utility vehicle 102 so that the soil sampler module 104 can be tilted as described (e.g., for maintenance). Two lateral conveyor belts 142 extend through the soil sampler module 104 proximate to the side drills 110 to the central conveyor belt 136. In embodiments of the disclosure, the conveyor system 134 includes one or more guides 144 positioned to guide cores along the lateral conveyor belt 142. A core is deposited from the side drill 110 onto the lateral conveyor belt 142, which feeds the core onto the central conveyor belt 136. The core is then fed into the cab 106 of the utility vehicle 102 and provided to a bag transition 146. A soil collection bag is placed under the bag transition 146 to collect the core. In embodiments of the disclosure, differently sized and/or shaped bag transitions 146 can be provided for differently configured soil collection bags. Further, in some embodiments, a cover formed from a solid, transparent plastic material is provided over the central conveyor belt 136 in the cab 106 of the utility vehicle 102 so that an operator can verify that the core has been collected and deposited in the soil collection bag.

In some embodiments, the soil sampler module 104 includes one or more power sprockets 148 and one or more drive sprockets 150. The ratio of the power sprocket 148 to the drive sprocket 148 is about two-to-one (2:1). For instance, the power sprocket 148 comprises thirty-two (32) teeth and the drive sprocket 148 comprises about sixteen (16) teeth. In this manner, the motor powering the conveyor system 134 can be run more slowly with respect to the speed of the conveyor system 134. Thus, heat generated by the motor can be reduced, while fuel consumption can be improved. A tensioner 152 is also included for tensioning the drive sprocket 148 and the drive sprocket 148.

In some embodiments, the soil sampler assembly 100 includes one or more cameras to monitor operations of the soil sampler assembly 100. For example, the soil sampler assembly 100 can include a backup camera, and/or cameras configured to capture images (e.g., still images, video) of one or more of the conveyors of the conveyor system 134, and so forth. A monitor can be included in the cab 106 of the utility vehicle 102 to display images captured by the one or more cameras. Further, the utility vehicle 102 can include an instrument rail configured to place controls, monitors, and so forth for the soil sampler assembly 100 in reach of the operator.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A soil sampler assembly comprising:
   a utility vehicle, the utility vehicle comprising a cab;
   a soil sampler module coupled to the utility vehicle, the soil sampler module configured to deposit a soil sample in the cab;
   a probe and a transfer block coupled to the soil sampler, the transfer block configured to vibrate the probe when sampling soil; and a conveyor system configured to convey the soil sample to the cab, the conveyor system including a central conveyor belt and a lateral conveyor belt that feeds the central conveyor belt.

2. The soil sampler assembly as recited in claim 1, wherein the utility vehicle comprises a diesel powered power vehicle.

3. The soil sampler assembly as recited in claim 1, wherein the central conveyor belt is on a travel track.

4. The soil sampler assembly as recited in claim 1, wherein the soil sampler module comprises a power sprocket for powering the conveyor system and a drive sprocket for driving a conveyor of the conveyor system, and a ratio of the power sprocket to the drive sprocket is about two-to-one (2:1).

5. The soil sampler assembly as recited in claim 1, further comprising a sampler arm assembly, wherein the sampler arm assembly is supported by at least one of the utility vehicle or the soil sampler module.

6. The soil sampler assembly as recited in claim 5, wherein the sampler arm assembly comprises an auger.

7. The soil sampler assembly as recited in claim 5, wherein the sampler arm assembly comprises a proximity switch.

8. The soil sampler assembly as recited in claim 1, wherein the probe is configured to obtain a core comprising the soil sample.

9. The soil sampler assembly as recited in claim 8, wherein the probe tapers to define a tip comprising an outer surface defining an outer taper bore and an inner surface defining an inner taper bore.

10. The soil sampler assembly as recited in claim 9, wherein a ratio of an inside diameter of the inner surface distal to the end of the tip to an inside diameter of the inner surface proximal to the end of the tip is between about two-to-one (2:1) and about one and two-thirds-to-one (1.67:1), and the inner surface of the inner taper bore extends farther with respect to the length of the probe than the outer surface of the outer taper bore.

11. The soil sampler assembly as recited in claim 9, wherein the soil sampler module comprises a brush positioned proximate to the tip of the probe when the probe is oriented in a generally vertical orientation.

12. The soil sampler assembly as recited in claim 1, further comprising a self-resetting knockout peg assembly configured to at least one of eject the soil sample from the soil sampler module onto the conveyor system or perform a reset operation when the soil sample contacts a knockout peg but is not ejected from the soil sampler module.

13. A soil sampler assembly comprising:
a diesel powered power vehicle including a cab;
a soil sampler module coupled to the diesel powered power vehicle, the soil sampler module configured to deposit a soil sample in the cab;
a conveyor system configured to convey the soil sample to the cab, the conveyor system including a central conveyor belt and a lateral conveyor belt; and
a sampler arm assembly coupled to the soil sampler module, the sampler arm assembly configured to collect the soil sample, the sampler arm assembly including a probe and a transfer block coupled to the soil sampler, the transfer block configured to vibrate the probe when sampling soil.

14. The soil sampler assembly as recited in claim 13, wherein the soil sampler module comprises a power sprocket for powering the conveyor system and a drive sprocket for driving a conveyor of the conveyor system, and a ratio of the power sprocket to the drive sprocket is about two-to-one (2:1).

15. The soil sampler assembly as recited in claim 13, wherein the soil sampler module comprises a power sprocket for powering the conveyor system and a drive sprocket for driving a conveyor of the conveyor system, and a ratio of the power sprocket to the drive sprocket is about two-to-one (2:1), wherein the sampler arm assembly comprises a drill, wherein the drill comprises a probe configured to obtain a core comprising the soil sample, and wherein the probe comprises a tip including an outer surface defining an outer taper bore and an inner surface defining an inner taper bore, wherein a ratio of an inside diameter of the inner surface distal to the end of the tip to an inside diameter of the inner surface proximal to the end of the tip is between about two-to-one (2:1) and about one and two-thirds-to-one (1.67:1).

16. The soil sampler assembly as recited in claim 13, further comprising a knockout peg assembly configured to eject the soil sample from the soil sampler module onto the conveyor system, wherein the knockout peg assembly is configured to extend a shaft into a tip of the probe.

\* \* \* \* \*